United States Patent [19]

Nickolson et al.

[11] Patent Number: 4,532,236
[45] Date of Patent: Jul. 30, 1985

[54] CERTAIN PROSTACYCLINS AND THEIR BLOOD-PRESSURE-LOWERING AND THROMBOCYTE-AGGREGATION-INHIBITING COMPOSITIONS AND METHODS

[75] Inventors: Robert Nickolson; Helmut Vorbrueggen, both of Berlin; Jorge Casals-Stenzel, Mainz; Martin Haberey, Berlin, all of Fed. Rep. of Germany

[73] Assignee: Schering Aktiengesellschaft, Berlin and Bergkamen, Fed. Rep. of Germany

[21] Appl. No.: 531,898

[22] PCT Filed: Nov. 25, 1982

[86] PCT No.: PCT/DE82/00222
§ 371 Date: Jul. 27, 1983
§ 102(e) Date: Jul. 27, 1983

[87] PCT Pub. No.: WO83/01951
PCT Pub. Date: Jun. 9, 1983

[30] Foreign Application Priority Data

Nov. 27, 1981 [DE] Fed. Rep. of Germany ....... 3147714

[51] Int. Cl.$^3$ .................. A61K 31/34; A61K 31/557; C07D 307/935
[52] U.S. Cl. ............................ 514/184; 514/337; 514/422; 514/444; 514/451; 514/459; 514/469; 546/269; 548/525; 549/60; 549/214; 549/420; 549/465
[58] Field of Search .................. 549/214, 420, 465, 60; 542/426, 429; 424/285, 184, 263, 274, 275, 283; 546/269; 548/525

[56] References Cited

U.S. PATENT DOCUMENTS 4,256,883 3/1981 Nicolaori et al. ................... 549/465

Primary Examiner—Henry R. Jiles
Assistant Examiner—Bernard I. Dentz
Attorney, Agent, or Firm—Millen & White

[57] ABSTRACT

Prostacyclin derivatives of general Formula I

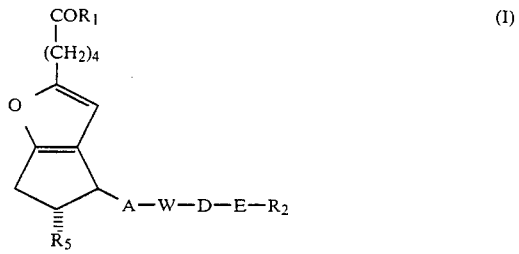

wherein
$R_1$ is the residue $OR_3$ wherein $R_3$ means hydrogen or alkyl of 1-10 carbon atoms substituted, if desired, by halogen, aryl, $C_1$-$C_4$-alkoxy, or $C_1$-$C_4$-dialkylamino; cycloalkyl, aryl, or a heterocyclic residue; or is the residue $NHR_4$ wherein $R_4$ means hydrogen, an alkanoyl residue, or an alkanesulfonyl residue of respectively 1-10 carbon atoms,
A is a —$CH_2$—$CH_2$— or trans—CH=CH—group,
W is

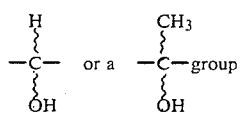

wherein the OH-group can be respectively esterified with a benzoyl or alkanoic acid residue of 1-4 carbon atoms, or can be etherified with a tetrahydropyranyl, tetrahydrofuranyl, $C_1$-$C_4$-alkoxyalkyl, or tri($C_1$-$C_4$-alkyl)-silyl residue, wherein the free or esterified OH-group can be in the α- or β-position,
D and E jointly mean a direct bond or
D is a straight-chain or branched alkylene group of 1-5 carbon atoms,
E is an oxygen atom or a direct bond,
$R_2$ is a straight-chain or branched-chain alkyl group of 1-6 carbon atoms, a straight-chain or branched-chain alkenyl group of 2-6 carbon atoms which can be substituted by phenyl, halogen, or $C_1$-$C_4$-alkyl and, if D and E jointly represent a direct bond, is an alkynyl residue of 2-6 carbon atoms optionally substituted in the 1-position by halogen or $C_1$-$C_4$-alkyl,
$R_5$ is a hydroxy group which can be esterified with an alkanoic acid residue of 1-4 carbon atoms or which can be etherified with a tetrahydropyranyl, tetrahydrofuranyl, alkoxyalkyl, or trialkylsilyl residue and, if $R_3$ is hydrogen, the salts thereof with physiologically compatible bases, and a process for the preparation thereof.

The compounds exhibit blood-pressure-lowering and thrombocyte-aggregation-inhibiting activity.

26 Claims, No Drawings

CERTAIN PROSTACYCLINS AND THEIR BLOOD-PRESSURE-LOWERING AND THROMBOCYTE-AGGREGATION-INHIBITING COMPOSITIONS AND METHODS

BACKGROUND OF THE INVENTION

The invention relates to novel prostacyclin derivatives, a process for the preparation thereof, as well as use thereof as medicinal agents.

Prostacyclin ($PGI_2$), one of the primary factors in blood platelet aggregation, has a dilating effect on various blood vessels (Science 196:1072) and thus could be considered as an agent for lowering blood pressure. However, $PGI_2$ does not possess the stability required for a medicinal agent. Thus, its half-life at physiological pH values and at room temperature is merely a few minutes.

SUMMARY OF THE INVENTION

It has been found that aromatization of the tetrahydrofuran ring in the prostacyclin leads to stabilization of the prostacyclin molecule, the pharmacological spectrum of activity being preserved while the duration of effectiveness of the novel prostacyclins is markedly prolonged.

The compounds of this invention have blood-pressure-lowering and bronchodilatory effects. They are furthermore suitable for inhibiting thrombocyte aggregation, vasodilation, and gastric acid secretion.

The invention relates to prostacyclins of general Formula I

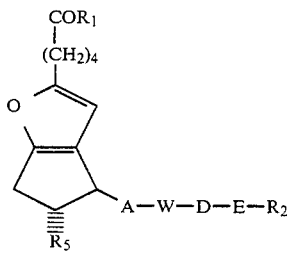

wherein $R_1$ is the residue $OR_3$ wherein $R_3$ means hydrogen or alkyl of 1-10 carbon atoms substituted, if desired, by halogen, aryl, $C_1$-$C_4$-alkoxy, or $C_1$-$C_4$-dialkylamino; cycloalkyl, aryl, or a heterocyclic residue; or is the residue $NHR_4$ wherein $R_4$ means hydrogen, an alkanoyl residue, or an alkanesulfonyl residue of respectively 1-10 carbon atoms, A is a —$CH_2$—$CH_2$— or trans—CH=CH—group, W is a

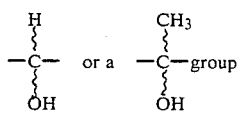

wherein the OH-group can be respectively esterified with a benzoyl or alkanoic acid residue of 1-4 carbon atoms, or can be etherified with a tetrahydropyranyl, tetrahydrofuranyl, $C_1$-$C_4$-alkoxyalkyl, or tri-($C_1$-$C_4$-alkyl)-silyl residue, wherein the free or esterified OH-group can be in the α- or β-position, D and E jointly mean a direct bond or D is a straight-chain or branched alkylene group of 1-5 carbon atoms, E is an oxygen atom or a direct bond, $R_2$ is a straight-chain or branched-chain alkyl group of 1-6 carbon atoms, a straight-chain or branched-chain alkenyl group of 2-6 carbon atoms which can be substituted by phenyl, halogen, or $C_1$-$C_4$-alkyl and, if D and E jointly represent a direct bond, is an alkynyl residue of 2-6 carbon atoms optionally substituted in the 1-position by halogen or $C_1$-$C_4$-alkyl, $R_5$ is a hydroxy group which can be esterified with an alkanoic acid residue of 1-4 carbon atoms or which can be etherified with a tetrahydropyranyl, tetrahydrofuranyl, alkoxyalkyl, or trialkylsilyl residue and, if $R_3$ is hydrogen, the salts thereof with physiologically compatible bases.

DETAILED DISCUSSION

The alkyl group $R_3$ can be linear or branched alkyl groups of 1-10 carbon atoms, such as, for example, methyl, ethyl, propyl, butyl, isobutyl, tert-butyl, pentyl, neopentyl, heptyl, hexyl, decyl. The alkyl groups $R_3$ can optionally be mono- to polysubstituted by halogen atoms, alkoxy groups of 1-4 carbon atoms, optionally substituted aryl groups, dialkylamines, and trialkylammonium of 1-4 carbon atoms. Monosubstituted alkyl groups are preferred. Examples for substituents are fluorine, chlorine, or bromine atoms, phenyl, dimethylamine, methoxy, ethoxy. Preferred alkyl groups $R_3$ are those of 1-4 carbon atoms, such as, for example, methyl, ethyl, propyl, dimethylaminopropyl, isobutyl, and butyl.

Suitable aryl groups $R_3$ are substituted as well as unsubstituted aryl groups, such as, for example, phenyl, 1-naphthyl, and 2-naphthyl, each of which can be substituted by 1-3 halogen atoms, a phenyl group, 1-3 alkyl groups of respectively 1-4 carbon atoms, a chloromethyl, fluoromethyl, trifluoromethyl, carboxy, hydroxy, or alkoxy group of 1-4 carbon atoms. The substituents in the 3- and 4-positions on the phenyl ring are preferred, for example, by fluorine, chlorine, alkoxy, or trifluoromethyl or in the 4-position by hydroxy.

The cycloalkyl group $R_3$ can contain, in the ring, 4-10, preferably 4-6 carbon atoms. The rings can be substituted by alkyl groups of 1-4 carbon atoms. Examples that can be cited are cyclobutyl, cyclopentyl, cyclohexyl, methylcyclohexyl, and adamantyl.

Suitable as heterocyclic groups $R_3$ are 5- and 6-membered heterocycles, among which those with a hetero atom, such as, for example, nitrogen, oxygen, or sulfur, are especially preferred. Examples are: 2-furyl, 2-thienyl, 3-thienyl, 2-pyridyl, 3-pyridyl, 4-pyridyl, etc.

The acid residue $R_4$ can be constituted by physiologically compatible acid residues. Preferred acids are organic carboxylic acids and sulfonic acids of 1-15 carbon atoms pertaining to the aliphatic, cycloaliphatic, aromatic, aromatic-aliphatic, and heterocyclic series. These acids can be saturated, unsaturated and/or polybasic and/or substituted in the usual way. Examples for substituents that can be mentioned are alkyl, hydroxy, alkoxy, oxo, or amino groups, or halogen atoms.

The following carboxylic acids are cited as examples: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di- and trichloroacetic acid, aminoacetic acid, diethylaminoacetic acid, piperidinoacetic acid, morpholinoacetic acid, lactic acid, succinic acid, adipic acid, benzoic acid, benzoic acids substituted with halogen, trifluoromethyl, hydroxy, alkoxy, or carboxy groups, nicotinic acid, isonicotinic acid, furan-2-carboxylic acid, cyclopentylpropionic acid. Especially preferred acyl residues are those of up to 10 carbon atoms.

Suitable sulfonic acids are, for example, alkanesulfonic acids of 1-10 carbon atoms, such as methanesulfonic acid, ethanesulfonic acid, isopropanesulfonic acid, β-chloroethanesulfonic acid, butanesulfonic acid, cyclopentanesulfonic acid, cyclohexanesulfonic acid, but also benzenesulfonic acid, p-toluenesulfonic acid, p-chlorobenzenesulfonic acid, N,N-dimethylaminosulfonic acid, N,N-diethylaminosulfonic acid, N,N-bis(β-chloroethyl)aminosulfonic acid, N,N-diisobutylaminosulfonic acid, N,N-dibutylaminosulfonic acid, pyrrolidino-, piperidino-, piperazino-, N-methylpiperazino-, and morpholinosulfonic acid.

The hydroxy groups $R_5$ and those in W can be functionally modified, for example by etherifying or esterifying; the free or modified hydroxy groups in W can be in the α-or β-position; free hydroxy groups are preferred. Suitable ether and acyl residues are those known to persons skilled in the art. Ether residues that can be easily split off are preferred, such as, for example, the tetrahydropyranyl, tetrahydrofuranyl, α-ethoxyethyl, trimethylsilyl, dimethyl-tert-butylsilyl, and tribenzylsilyl residues. Suitable acyl residues are $C_1$–$C_4$-alkanoyl residues, such as, for example, acetyl, propionyl, butyryl, or benzoyl.

The alkyl and alkenyl groups $R_2$ can be straight-chain and branched-chain alkyl residues of 1–10 carbon atoms and alkenyl residues of 2–10, especially 1–6, or 2–6 carbon atoms, respectively, which can be substituted, if desired, by optionally substituted phenyl, alkyl of 1–4 carbon atoms, or halogen. Examples that can be cited are methyl, ethyl, propyl, butyl, isobutyl, tert-butyl, pentyl, hexyl, heptyl, octyl, butenyl, isobutenyl, propenyl, pentenyl, hexenyl, as well as benzyl and, in case D and E jointly mean a direct bond, alkynyl of 2–6 carbon atoms optionally substituted in the 1-position by fluorine or $C_1$–$C_4$-alkyl. Suitable alkynyl residues are: ethynyl, propyn-1-yl, propyn-2-yl, 1-methylpropyn-2-yl, 1-fluoropropyn-2-yl, 1-ethylpropyn-2-yl, 1-fluorobutyn-2-yl, butyn-2-yl, butyn-3-yl, 1-methylbutyn-3-yl, 1-methylpentyn-3-yl, 1-fluoropentyn-3-yl, 1-methylpentyn-2-yl, 1-fluoropentyn-2-yl, 1-methylpentyn-4-yl, 1-fluoropentyn-4-yl, hexyn-1-yl, 1-methylhexyn-2-yl, 1-fluorohexyn-2-yl, 1-methylhexyn-3-yl, 1-methylhexyn-4-yl, hexyn-3-yl, 1,1-dimethylpropyn-2-yl, 1,1-dimethylbutyn-3-yl, 1,1-dimethylpentyn-3-yl, 1,1-dimethylpentyn-4-yl, 1,1-dimethylhexyn-3-yl, 1,1-dimethylhexyn-4-yl, etc. Halogen as substituent for the alkyl and alkenyl groups $R_2$ can be bromine, chlorine, and fluorine. Chlorine and fluorine are preferred.

Suitable for the alkylene group D are straight-chain or branched-chain alkylene residues which can contain a double bond, but preferably saturated ones of 1–10, especially 1–5 carbon atoms; these can optionally be substituted by fluorine atoms or $C_1$–$C_4$-alkyl, especially in the 1- or 2-position. Examples are: methylene, fluoromethylene, ethylene, 1,2-propylene, ethylethylene, trimethylene, tetramethylene, pentamethylene, 1-methyltetramethylene, 1-methyltrimethylene, 2-methyltrimethylene, 2-methyltetramethylene, 1,1-trimethylenethylene, 1,2-methylenethylene. If a double bond is present, it is in the 2-, 3-, or 4-position in the alkylene residues of 4–10 carbon atoms.

Suitable for salt formation with the free acids ($R_3$=H) are inorganic and organic bases as known to one skilled in the art for the formation of physiologically compatible salts.

Examples are: alkali hydroxides, such as sodium and potassium hydroxide, alkaline earth hydroxides, such as calcium hydroxide, ammonia, amines, such as ethanolamine, diethanolamine, triethanolamine, N-methylglucamine, morpholine, tris(hydroxymethyl)methylamine, etc.

The invention furthermore concerns a process for the preparation of the prostacyclins of general Formula I of this invention, characterized by reacting a compound of general Formula II

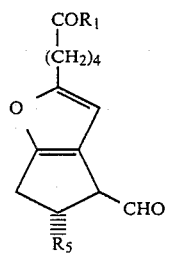

wherein $R_1$ and $R_5$ have the meanings given above, with an alkali salt of the phosphonate of general Formula III

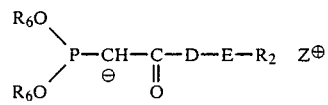

wherein
D, E, and $R_2$ have the meanings given above and
$R_6$ is $C_1$–$C_4$-alkyl and
Z represents the alkali metals Li, Na, or K,
and, depending on the desired significance, reducing the product or reacting the product with methylmagnesium bromide or with methyllithium, or optionally separating the product into the stereoisomers or saponifying the 1-ester or esterifying the 1-acid or reacting the latter with an isocyanate of the formula $R_4$—N=C=O wherein $R_4$ has the meaning given above, or splitting off OH-blocking groups.

The reaction of the compound of general Formula II with compounds of Formula III is effected at temperatures of −50° to 50° C., preferably at −30° to 20° C., in an organic solvent, preferably dimethoxyethane, within 0.5–10 hours under inert gas (such as, for example, $N_2$ or Ar) and under agitation.

The saponification of the prostacyclin esters is conducted according to methods known to a person skilled in the art, for example with alkaline catalysts. The introduction of the ester group wherein $R_3$ is an alkyl group of 1–10 carbon atoms takes place according to methods known to those skilled in the art. The carboxy compounds, for example, are reacted conventionally with diazohydrocarbons. The esterification with diazohydrocarbons is accomplished, for example, by mixing a solution of the diazohydrocarbon in an inert solvent, preferably in diethyl ether, with the carboxy compound in the same or in another inert solvent, e.g. methylene chloride. After the reaction has been completed within 1–30 minutes, the solvent is removed and the ester is purified as usual. Diazoalkanes are either known or can be prepared according to known methods [Org. Reactions 8:389–394 (1954)].

The ester group $OR_3$ wherein $R_3$ is a substituted or unsubstituted aryl group is introduced for $R_1$ according to methods known to those skilled in the art. For example, the carboxy compounds are reacted with the corresponding arylhydroxy compounds with dicyclohexylcarbodiimiide in the presence of a suitable base, for example pyridine or triethylamine, in an inert solvent. Suitable solvents are methylene chloride, ethylene chloride, chloroform, ethyl acetate, tetrahydrofuran, preferably chloroform. The reaction is conducted at temperatures of between $-30°$ C. and $+50°$ C., preferably at $+10°$ C.

The prostacyclin derivatives of general Formula I wherein $R_3$ means a hydrogen atom can be converted into salts with suitable amounts of the corresponding inorganic bases under neutralization. For example, when dissolving the corresponding PG acids in water containing the stoichiometric quantity of the base, the solid inorganic salt is obtained after evaporation of the water or after adding a water-miscible solvent, e.g. alcohol or acetone.

In order to produce an amine salt, which is done as usual, the prostacyclin of Formula I is dissolved, for example, in a suitable solvent, e.g. ethanol, acetone, acetonitrile, diethyl ether, or benzene, and at least the stoichiometric amount of the amine is added to this solution. In this process, the salt is ordinarily obtained in the solid form, or it is isolated in the usual way after evaporation of the solvent.

The functional modification of the free OH-groups takes place according to methods known to those skilled in the art. In order to introduce the ether blocking groups, for example, the reaction is performed with dihydropyran in methylene chloride, benzene, or chloroform with the use of an acidic catalyst, e.g. $POCl_3$, p-toluenesulfonic acid, or anhydrous mineral acids. The dihydropyran is used in excess, preferably in two to ten times the amount required theoretically. The reaction is normally completed at 0° C. to 30° C. after 15–30 minutes.

The acyl blocking groups are introduced by reacting a compound of general Formula I in a manner known per se with a carboxylic acid derivative, e.g. an acid chloride, acid anhydride, etc., in the presence of a tertiary amine base, such as, for example, pyridine, dimethylaminopyridine, etc.

The liberation of a functionally modified OH-group to obtain the compounds of general Formula I takes place according to known methods. For example, the ether blocking groups are split off in an aqueous solution of an organic acid, such as, for example, acetic acid, propionic acid, etc., or in an aqueous solution of an inorganic acid, e.g. hydrochloric acid. To improve solubility, a water-miscible, inert organic solvent is suitably added. Organic solvents that can be used are, for example, alcohols, such as methanol and ethanol, and ethers, such as dimethoxyethane, dioxane, and tetrahydrofuran. Tetrahydrofuran is preferably employed. The splitting-off step is preferably conducted at temperatures of between 20° C. and 80° C.

The silyl ether blocking groups are split off, for example, with tetrabutylammonium fluoride or with KF in the presence of a crown ether. Examples for suitable solvents are tetrahydrofuran, diethyl ether, dioxane, methylene chloride, etc. The splitting-off step is preferably effected at temperatures of between 0° C. and 80° C.

The acyl groups are saponified, for example, with alkali or alkaline earth carbonates or hydroxides in an alcohol or in the aqueous solution of an alcohol. Suitable alcohols are aliphatic alcohols, such as, for example, methanol, ethanol, butanol, etc., preferably methanol. Suitable alkali carbonates and hydroxides are potassium and sodium salts, but the potassium salts are preferred. Examples for suitable alkaline earth carbonates and hydroxides are calcium carbonate, calcium hydroxide, and barium carbonate. The reaction takes place at $-10°$ C. to 70° C., preferably at 25° C.

The reaction of the compound of general Formula I wherein $R_3$ means a hydrogen atom with an isocyanate of the general formula $$R_4-N=C=O$$

wherein $R_4$ has the meaning indicated above, takes place optionally with the addition of a tertiary amine, such as triethylamine or pyridine, for example. The reaction can be conducted without a solvent or in an inert solvent, preferably acetonitrile, tetrahydrofuran, acetone, dimethylacetamide, methylene chloride, diethyl ether, benzene, toluene, dimethyl sulfoxide, at temperatures of above or below room temperature, e.g. between $-80°$ C. and 100° C., preferably at 0°–30° C.

The compounds of general Formula II serving as the starting material can be produced analogously to the disclosure in Examples 1–14. Analogously to Examples 4 and 6, the corresponding sulfur compounds can be produced and can be converted in an analogous reaction to the compound in Example 5 or to the corresponding sulfur compound in Example 7.

Methods known to those skilled in the art are used for the oxidation of the 4-hydroxymethyl group in the compounds of Formula IV

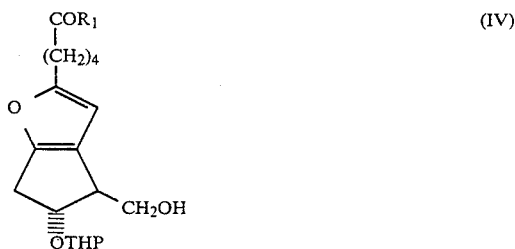

wherein
$R_1$ has the meanings given above and
THP is a tetrahydropyranyl residue,
to the aldehydes of general Formula V

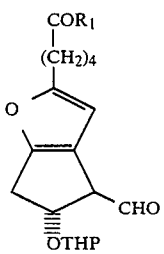

(V)

wherein R₁ and THP have the above-indicated meanings.

Suitable oxidizing agents or methods are, for example: Collins reagent (Tetrahedron Letters, 1968:3368), Jones reagent (J. Chem. Soc. 1953:2555), pyridinium chlorochromate (Tetrahedron Letters, 1975:2647), pyridinium dichromate (Tetrahedron Letters, 1979:399), or the Moffat-Pfitzner method. The oxidation is conducted with Collins reagent at −20° to +30° C., preferably at 0°–5° C., or with Jones reagent at −40° to +30° C., preferably −30° to 0° C., or with pyridinium chlorochromate or pyridinium dichromate at −20° to +40° C., preferably at 20°–30° C. in a solvent inert with respect to oxidizing agents. Depending on the reagent employed, the solvents used can be methylene chloride, chloroform, ethylene chloride, dimethylformamide, pyridine, etc.

If end products are desired in the final analysis which contain free hydroxy groups, starting compounds are advantageously utilized wherein these groups are blocked intermediarily by preferably readily cleavable ether or acyl residues.

The compounds of this invention have blood-pressure-lowering and bronchodilatory effects. They are furthermore suitable for inhibiting thrombocyte aggregation. Consequently, the novel prostacyclin derivatives of Formula I represent valuable pharmaceutically active agents. Moreover, with a similar spectrum of activity, they exhibit a higher specificity as compared with corresponding prostaglandins and, above all, a substantially longer efficacy. As compared with PGI₂, they are distinguished by higher stability. The high tissue specificity of the novel prostaglandins is demonstrated in a study on smooth-muscle organs, such as, for example, on the guinea pig ileum or on the isolated rabbit trachea, where a substantially lower stimulation can be observed than in the administration of natural prostaglandins of the E-, A-, or F-type.

The novel prostaglandin analogs exhibit the properties typical for prostacyclins, such as, for example, lowering of peripheral arterial and coronary vascular resistance, inhibition of thrombocyte aggregation and dissolution of platelet thrombi, myocardial cytoprotection and thus lowering of systemic blood pressure without simultaneously lowering stroke volume and coronary blood flow; treatment for stroke, prophylaxis and therapy of coronary heart disease, coronary thrombosis, cardiac infarction, peripheral arterial diseases, arteriosclerosis and thrombosis, prophylaxis and therapy of ischemic attacks of the CNS system, therapy for shock, inhibition of bronchoconstriction, inhibition of gastric acid secretion and cytoprotection for gastric and intestinal mucosa, as well as cytoprotection in liver and pancreas; antiallergic properties, lowering of pulmonary vascular resistance and pulmonary blood pressure, promotion of kidney blood flow, utilization in place of heparin or as adjuvant in dialysis of hemofiltration, preservation of blood plasma stores, especially blood platelet stores, inhibition of labor, treatment of gestational toxicosis, enhancement of cerebral blood flow, etc. Besides, the novel prostaglandin analogs exhibit antiproliferative properties. The novel prostacyclins can also be utilized in combination, for example, with β-blockers or diuretics.

The dosage of the compounds is 1–1,500 μg/kg/day, if administered to human patients. The unit dosage for the pharmaceutically acceptable carrier is 0.01–100 mg.

With intravenous injection administered to non-anesthetized, hypertonic rats in doses of 5, 20, and 100 μg/kg body weight, the compounds of this invention exhibit a stronger blood-pressure-lowering effect and a more prolonged duration of efficacy than PGE₂ and PGA₂ without triggering diarrhea, as does PGE₂, or cardiac arrhythmias, as does PGA₂.

Upon intravenous injection administered to narcotized rabbits, the compounds of this invention show, as compared with PGE₂ and PGA₂, a stronger and also considerably prolonged blood-pressure-lowering effect without affecting other smooth-muscle organs or organ functions.

Sterile, injectable, aqueous or oily solutions are used for parenteral administration. Suitable for oral administration are, for example, tablets, dragees, or capsules.

Accordingly, the invention likewise concerns medicinal agents based on the compounds of general Formula I and conventional auxiliary agents and excipients.

The active agents of this invention are to serve, for example, for the production of blood-pressure-lowering agents in conjunction with the auxiliary agents known and customary in galenic pharmacy.

The present invention also relates to prostacyclin intermediates of general Formula VI

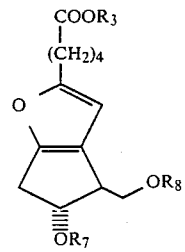

(VI)

wherein
R₃ has the meanings given above and
R₇ and R₈ mean the blocking groups set forth for R₅, a tri-(C₁–C₄)-alkylsilyl group, or a benzyl group, and to a process for the preparation of compounds of Formula VI

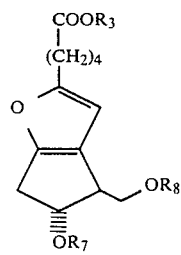

(VI)

wherein $R_3$, $R_7$, and $R_8$ have the meanings given above, characterized by treating compounds of general Formula VII

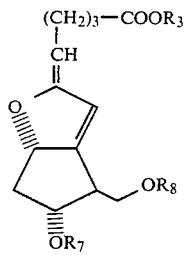

(VII)

wherein $R_3$, $R_7$, and $R_8$ have the meanings indicated above, with weak Lewis acids at an elevated temperature.

It is known from prostacyclin that it loses its pharmacological activity within minutes by conversion into the corresponding 6-ketoprostaglandin. (S. Moncada and J. R. Vane in Biochemical Aspects of Prostaglandins and Thromboxanes, N. Kharasch and J. Fried (editors), Academic Press, New York, 1977, pages 155 et seq.)

The dienols of Formula VII likewise represent relatively unstable compounds and decompose under the mere effects of air and traces of water. By heating in the presence of weak Lewis acids, such as, for example, magnesium sulfate, boric acid, $(NH_4)_2SO_4$, $NH_4Cl$, silica gel, $Al_2O_3$, Al tris(isopropylate), or weak organic acids, the dienols VII can be surprisingly converted into the stable furanprostacyclins of Formula VI.

Aromatization is effected in dry, inert organic aprotic solvents, such as benzene, toluene, xylene, tetrahydrofuran, dioxane, diglyme, ether, hexamethyldisilazane, or trimethylsilyl diethylamine at 30°–200° C., preferably 50°–130° C.

EXAMPLE 1

(1S,5R,6S,7R)-6-tert-Butyldimethylsilyloxymethyl-7-benzoyloxy-2-oxabicyclo[3.3.0]octan-3-one A solution of 11.052 g of (1S,5R,6S,7R)-6-hydroxymethyl-7-benzoyloxy-2-oxabicyclo[3.3.0]octan-3-one (DOS No. 2,610,718) in 54.0 ml of absolute dimethylformamide is combined with 3.03 g of imidazole and 6.63 g of tert-butyldimethylsilyl chloride, and the mixture is stirred for 3 hours at room temperature. The solution is subsequently precipitated into 500 ml of ice water, the precipitate is suctioned off, and the residue is dissolved in methylene chloride. The organic solution is dried over magnesium sulfate and concentrated. The crude product is recrystallized from hexane, thus obtaining 15.30 g of the title compound, mp 75.8° C.

EXAMPLE 2

(1S,5R,6S,7R)-6-tert-Butyldimethylsilyloxymethyl-7-hydroxy-2-oxabicyclo[3.3.0]octan-3-one 1.845 g of anhydrous potassium carbonate is introduced into a solution of 11.716 g of the silyl ether produced in Example 1 in 122 ml of absolute MeOH, and the mixture is agitated under argon for 3 hours. The reaction solution is then cooled in an ice bath and gently combined dropwise with 1.86 ml of concentrated hydrochloric acid. Excess methanol is extensively concentrated under vacuum at room temperature, the residue is combined with 300 ml of methylene chloride, and the solution is dried over magnesium sulfate, filtered off, and concentrated. The oily residue is made to crystallize by trituration with hexane, thus obtaining 6.562 g of the title compound, mp 60.7° C.

Chromatography of the mother liquors over 100 g of silica gel in a methylene chloride/25% acetone-methylene chloride gradient and crystallization from hexane yield another 1.089 g of the title compound, mp 62.3° C.

EXAMPLE 3

(1S,5R,6S,7R)-6-tert-Butyldimethylsilyloxymethyl-7-(tetrahydropyran-2-yloxy)-2-oxabicyclo[3.3.0]octan-3-one A solution of 9.608 g of the diol described in Example 2 in 134 ml of absolute methylene chloride is combined with 4.08 ml of 2,3-dihydro-4H-pyran and 56.3 mg of p-toluenesulfonic acid. After 20 minutes, the reaction is terminated by adding 0.06 ml of triethylamine; excess methylene chloride is removed by vacuum distillation at room temperature, and the residue is chromatographed on 200 g of silica gel in a hexane/25% ethyl acetate-hexane gradient, thus producing 13.391 g of the title compound as an oil.

IR: 2940, 1760, 1450, 1340, 1245, 1160, 1110, 1060, 1030, 970, 835, 775 cm$^{-1}$.

EXAMPLE 4

(1S,4S,5R,6S,7R)-4-Phenylselenyl-6-tert-butyldimethylsilyloxymethyl-7-(tetrahydropyran-2-yloxy)-2-oxabicyclo[3.3.0]octan-3-one A solution of lithium hexamethyldisilazide is prepared by adding 50 ml of n-butyllithium solution (1.21-molar in hexane) dropwise to a solution of 12.5 ml of hexamethyldisilazane in 100 ml of absolute tetrahydrofuran cooled to −10° C., under argon. A solution, cooled to −70° C., of 18.55 g of the tetrahydropyranyl ether prepared according to Example 3 in 400 ml of absolute tetrahydrofuran is combined within 10 minutes with the freshly prepared solution of lithium hexamethyldisilazide under argon, and the mixture is further agitated for 10 minutes. Within 5 minutes, a solution of 11.45 g of phenylselenyl chloride in 105 ml of absolute tetrahydrofuran is added dropwise to this mixture, and after this addition has been completed, the solution is allowed to warm up to room temperature. The solution is combined with about 50 g of silica gel, excess solvent is removed by vacuum distillation, and the residue is purified by chromatography on silica gel with a hexane/15% ethyl acetate-hexane gradient, thus obtaining 15.41 g of the title compound.

IR: 2950, 1760, 1570, 1450, 1340, 1240, 1170, 1110, 1070, 1030, 835, 775, 740, 690 cm$^{-1}$.

EXAMPLE 5

(1S,6S,7R)-6-tert-Butyldimethylsilyloxymethyl-7-(tetrahydropyran-2-yloxy)-2-oxabicyclo[3.3.0]oct-4-en-3-one A mixture consisting of 81 ml of 30% hydrogen peroxide and 165 ml of water is added to a solution of 13.14 g of the phenylselenide produced in Example 4 in 375 ml of methylene chloride, and the mixture is stirred under argon for 1 hour at room temperature. After 1 hour, the reaction solution is diluted with ether, the aqueous phase is separated, and the organic phase is washed with water. The ether solution is dried over magnesium sulfate and concentrated under vacuum. The crude product is chromatographed over 200 g of silica gel in a hexane/15% ethyl acetate-hexane gradient, thus obtaining 8.66 g of the title compound as an oil.

IR: 2940, 1760, 1650, 1450, 1370, 1330, 1310, 1250, 1100, 1030, 950, 835, 775 cm$^{-1}$.

EXAMPLE 6

(1S,5S,6S,7R)-5-Phenylselenyl-6-tert-butyldimethylsilyloxymethyl-7-(tetrahydropyran-2-yloxy)-2-oxabicyclo[3.3.0]octan-3-one 6.45 g of diphenyldiselenide is introduced within 30 minutes in incremental portions into a suspension, cooled to 0° C., of 1.698 g of sodium borohydride in 41.6 ml of absolute ethanol. After the gas evolution has ceased, a solution of 7.20 g of the unsaturated lactone produced in Example 5 in 68 ml of absolute ethanol is added to the already prepared solution of sodium selenophenolate, and the mixture is stirred under argon for 1.5 hours at room temperature. The solution is then poured into 1.0 l of saturated sodium chloride-ice mixture, and the aqueous phase is extracted four times with 150 ml portions of ether. The ether solution is washed neutral with semisaturated sodium chloride solution, dried over magnesium sulfate, and concentrated to dryness under vacuum. The crude product is chromatographed over 500 g of silica gel in a hexane/12% ethyl acetate-hexane gradient, thus obtaining 6.265 g of the title compound.

IR: 2950, 1760, 1560 (weak), 1450, 1430, 1340, 1250, 1120, 1090, 1070, 970, 835, 775, 740, 690 cm$^{-1}$.

EXAMPLE 7

(1S,3RS,5S,6S,7R)-5-Phenylselenyl-6-tert-butyldimethylsilyloxymethyl-7-(tetrahydropyran-2-yloxy)-2-oxabicyclo[3.3.0]-3-ol A solution, cooled to −70° C., of 5.64 g of the lactone described in Example 6 in 137 ml of toluene is combined with 19.3 ml of Dibah-T solution (20% strength in toluene), and the mixture is stirred under argon for 0.5 hour. Then excess Dibah is destroyed by gently adding dropwise 1.0 ml of isopropanol and 9.63 ml of water, and the mixture is further agitated for 3 hours at room temperature. The white precipitate is vacuum-filtered, the residue washed with methylene chloride, the combined organic phases are dried over magnesium sulfate and thereafter concentrated. The crude product is chromatographed over 100 g of silica gel with a hexane/10% acetone-hexane gradient, yielding 5.15 g of the title compound.

IR: 3700, 2940, 1560, 1460, 1430, 1340, 1250, 1080 (broad), 1020, 835, 775, 735, 695 cm$^{-1}$.

EXAMPLE 8

(1S,2S,3S,4R)-2-[(EZ)-6-Methoxycarbonyl-2-hexenyl]-2-phenylselenyl-3-tert-butyldimethylsilyloxymethyl-4-(tetrahydropyran-2-yloxy)cyclopentan-1-ol A solution, cooled to −10° C., of 33.30 ml of hexamethyldisilazane in 110 ml of absolute tetrahydrofuran is combined with 144.35 ml of butyllithium solution (1.11-molar in hexane) under argon. The freshly prepared solution of lithiumhexamethyldisilazide is added within 5 minutes to a suspension of 35.24 g of carboxybutyltriphenylphosphonium bromide in 343 ml of tetrahydrofuran, and the mixture is stirred for 40 minutes. A solution of 5.03 g of the lactol produced in Example 7 in 305 ml of absolute tetrahydrofuran is added dropwise to this dark-red ylide solution, and after this addition is finished, the mixture is stirred under argon for 2 hours at 45° C. The solution is subsequently poured into 3 l of 2% strength sodium chloride solution and the mixture acidified to pH 5–4.5 by adding 10% citric acid solution. The aqueous phase is extracted five times with respectively 300 ml of ether, and the combined ether phases are extracted five times with respectively 40 ml of 2% sodium hydroxide solution. The alkaline extracts are combined, acidified to pH 4.5 with 10% citric acid solution, and repeatedly extracted with ether. The ether phases are dried over magnesium sulfate and concentrated. In order to obtain the methyl ester, the crude product is dissolved in 200 ml of ether and treated with an ether solution of diazomethane. Excess diazomethane is destroyed by the dropwise addition of glacial acetic acid, and the solution is concentrated under vacuum. The crude product is chromatographed over 300 g of silica gel in a hexane/15% ethyl acetate-hexane gradient, thus producing 5.01 g of the title compound as an oil.

IR: 3450, 2930, 1730, 1580, 1460, 1430, 1340, 1070 (broad), 1020, 835, 775, 740, 695 cm$^{-1}$.

EXAMPLE 9

(5RS)-5-Iodo-5-[(2RS,3aS,4S,5R,6aS)-3a-phenylselenyl-4-tert-butyldimethylsilyloxymethyl-5-(tetrahydropyran-2-yloxy)perhydrocyclopenta[b]-furan-2-yl]pentanoic Acid Methyl Ester A solution of 4.98 g of the olefin produced in Example 8 in 94.6 ml of ether is combined with a solution of 10 g of sodium bicarbonate in 169 ml of water, and the mixture is cooled to 3° C. Within 20 minutes, a solution of 4.25 g of iodine in 145 ml of ether is added dropwise to this two-phase mixture, and the solution is stirred at 2°–3° C. for 2.5 hours. Subsequently the phases are separated, and the aqueous solution is extracted with ether. The organic phases are combined, washed with 5% sodium thiosulfate solution and semisaturated sodium chloride solution. The ether solution is dried over magnesium sulfate and evaporated under vacuum. The crude product is chromatographed over 300 g of silica gel in a hexane/10% ethyl acetate-hexane gradient, thus obtaining 5.65 g of the title compound as an oil.

IR: 2930, 1730, 1580, 1430, 1350, 1240, 1120, 1020, 975, 835, 775, 740, 695 cm$^{-1}$.

EXAMPLE 10

(5RS)-5-Iodo-5-[(2RS,4S,5R,6aS)-4-tert-butyldimethylsilyloxymethyl-5-(tetrahydropyran-2-yloxy)-4,5,6,6a-tetrahydro-2H-cyclopenta[b]furan-2-yl]pentanoic Acid Methyl Ester A solution of 4.52 g of the iodine ether described in Example 9 in 150 ml of tetrahydrofuran is combined with 60 ml of 15% hydrogen peroxide solution, and the mixture is stirred for 1 hour under argon at room temperature. Then the solution is stirred into ice water, the aqueous solution is extracted in succession with ether (three times) and ethyl acetate (once), and the organic phases are combined and washed with semisaturated sodium chloride solution. The organic solution is dried over magnesium sulfate and concentrated under vacuum. The residue is chromatographed over 250 g of silica gel in a hexane/12% ethyl acetatehexane gradient, thus obtaining 3.33 g of the title compound as an oil.

IR: 2900, 1730, 1440, 1370, 1240, 1160, 1100, 1030, 965, 835, 775 cm$^{-1}$.

EXAMPLE 11

5-[(2EZ)-(4S,5R,6aS)-4-tert-Butyldimethylsilyloxymethyl-5-(tetrahydropyran-2-yloxy)-4,5,6,6a-tetrahydro-2H-cyclopenta[b]furan-2-ylidene]pentanoic Acid Methyl Ester A solution of 2.33 g of the iodine ether disclosed in Example 10 in 47 ml of benzene is combined with 2.23 ml of diazabicycloundecene and the mixture stirred for 2 hours under argon at 50° C. The reaction solution is diluted with ethyl acetate and washed three times with water. The organic phase is dried over magnesium sulfate and concentrated. The crude product (1.86 g) is used in the next stage without further purification.

IR: 2940, 1730, 1680, 1440, 1370, 1240, 1160, 1100, 1030, 965, 835, 775 cm$^{-1}$.

EXAMPLE 12

5-[(4S,5R)-4-tert-Butyldimethylsilyloxymethyl-5-(tetrahydropyran-2-yloxy)-5,6-dihydro-4H-cyclopenta[b]furan-2-yl]pentanoic Acid Methyl Ester A solution of 1.86 g of the dienol ether produced according to Example 11 in 180 ml of benzene is combined under argon with 5.52 g of magnesium sulfate (dried), and the mixture is maintained at reflux temperature for 2 hours. The solution is allowed to cool, the magnesium sulfate is suctioned off and washed with ethyl acetate. The filtrate is concentrated under vacuum and chromatographed on 150 g of silica gel in a hexane/10% ethyl acetate-hexane gradient, thus obtaining 1.20 g of the title compound as an oil.

IR: 2930, 1730, 1620 (weak), 1550, 1460, 1430, 1340, 1240, 1190, 1110, 1070, 1030, 980, 935, 775 cm$^{-1}$.

EXAMPLE 13

5-[(4S,5R)-4-Hydroxymethyl-5-(tetrahydropyran-2-yloxy)-5,6-dihydro-4H-cyclopenta[b]furan-2-yl]-pentanoic Acid Methyl Ester A solution of 900 mg of the furan derivative produced in Example 12 in 120 ml of absolute tetrahydrofuran is combined with 960 mg of tetrabutylammonium fluoride dissolved in 10 ml of tetrahydrofuran, and the mixture is stirred under argon at room temperature for 1 hour. Thereafter the reaction solution is precipitated into ice water, and the aqueous phase is extracted repeatedly with ether. The organic phases are combined, washed with water and then with semisaturated sodium chloride solution, dried over magnesium sulfate, and concentrated. The crude product is chromatographed over 60 g of silica gel in a hexane/20% acetone-hexane gradient, thus obtaining 648 mg of the title compound as an oil.

IR: 3900, 2920, 1720, 1620, 1540, 1430, 1340, 1190, 1130, 1060, 1030, 870, 805 cm$^{-1}$.

EXAMPLE 14

5-[(4R,5R)-4-Formyl-5-(tetrahydropyran-2-yloxy)-5,6-dihydro-4H-cyclopenta[b]furan-2-yl]pentanoic Acid Methyl Ester A solution of 590 mg of the alcohol prepared in Example 13 in 75 ml of methylene chloride is combined with 271 mg of sodium acetate and 534 mg of pyridinium chlorochromate, and the mixture is stirred under argon for 50 minutes. The mixture is combined with a solution of 0.25 ml of isopropanol and 0.5 ml of pyridine in 50 ml of ether and further stirred for 10 minutes. Subsequently 7.5 g of magnesium sulfate is introduced, the reaction solution is filtered, and the residue is washed with ether. The organic solution is applied directly to a 30 g silica gel column and eluted with a hexane/8% acetone-hexane gradient, thus obtaining 325 mg of the title compound as an oil.

IR: 2930, 2700 (weak), 1730, 1650 (weak), 1550, 1430, 1340, 1250, 1190, 1130, 1070, 1030, 960 (weak), 865, 815 cm$^{-1}$.

EXAMPLE 15

5-[(4R,5R)-4-[(E)-3-Oxo-1-octenyl]-5-(tetrahydropyran-2-yloxy)-5,6-dihydro-4H-cyclopenta[b]furan-2-yl]pentanoic Acid Methyl Ester A suspension of 53 mg of sodium hydride (50% in oil) in 10 ml of absolute dimethoxyethane is combined dropwise with a solution of 244 mg of dimethyl(2-oxoheptyl)phosphonate in 3.0 ml of absolute dimethoxyethane, and the mixture is stirred under argon at room temperature for 0.5 hour. The solution is cooled to −30° C., thus crystallizing the sodium salt of the phosphonate. A solution of 310 mg of the aldehyde described in Example 14 in 3.0 ml of absolute dimethoxyethane is added dropwise to this suspension, and the mixture is stirred for 90 minutes at −30° C. Subsequently the mixture is combined with a solution of 0.5 ml of glacial acetic acid in 3.0 ml of dimethoxyethane and diluted with ether. This solution is washed in succession with dilute sodium bicarbonate solution, water, and brine, dried over magnesium sulfate, and concentrated. The crude product (450 mg) is purified by means of preparative layer chromatography on five plates (20×40 cm, layer thickness=0.5 mm) in a chloroform-ether (8:2) system, thus producing 229 mg of the title compound.

IR: 2940, 1740, 1670, 1630, 1550, 1430, 1340, 1200, 1130, 1070, 1030, 980 cm$^{-1}$.

EXAMPLE 16

5-[(4R,5R)-4-[(3S)-(E)-3-Hydroxy-1-octenyl]-5-(tetrahydropyran-2-yloxy)-5,6-dihydro-4H-cyclopenta[b]furan-2-yl]pentanoic Acid Methyl Ester and 5-[(4R,5R)-4-[(3R)-(E)-3-Hydroxy-1-octenyl]-5-(tetrahydropyran-2-yloxy)-5,6-dihydro-4H-cyclopenta[b]furan-2-yl]pentanoic Acid Methyl Ester A solution of 198 mg of the ketone disclosed in Example 15 in 5.3 ml of absolute methanol is combined at −40° C. with 100 mg of sodium borohydride, and the mixture is stirred under argon for 0.5 hour. Then 0.14 ml of glacial acetic acid is added gently dropwise to the reaction solution, and the mixture is precipitated into ice water. The aqueous phase is extracted with ether, the organic extract is washed with dilute sodium bicarbonate solution and thereafter with semisaturated sodium chloride solution. The ether solution is dried over magnesium sulfate and concentrated under vacuum, thus obtaining a crude product (205 mg) consisting of a mixture of the 15-alcohols. In order to separate the 15-epimers, the mixture is purified by means of preparative layer chromatography on three plates (20×40 cm, layer thickness 0.5 mm) in a chloroform-ether (9:1) system, thus obtaining 81.6 mg of the 15α-alcohol (prostaglandin numbering);

IR: 3950, 2930, 1730, 1630 (weak), 1540, 1430, 1340, 1210, 1130, 1070, 1030, 965 cm$^{-1}$; and 87.4 mg of the corresponding 15β-alcohol;

IR: 3950, 2930, 1730, 1630 (weak), 1540, 1430, 1340, 1210, 1130, 1070, 1030, 965 cm$^{-1}$.

EXAMPLE 17

5-[(4R,5R)-4-[(3S)-(E)-3-Hydroxy-1-octenyl]-5-hydroxy-5,6-dihydro-4H-cyclopenta[b]furan-2-yl]pentanoic. Acid Methyl Ester (Furaprostacyclin Methyl Ester) and 5-[(4R,5R)-4-[(3R)-(E)-3-Hydroxy-1-octenyl]-5-hydroxy-5,6-dihydro-4H-cyclopenta[b]furan-2-yl]pentanoic Acid Methyl Ester A solution of 78.1 mg of the 15α-alcohol described in Example 17 is dissolved in 7.7 ml of a tetrahydrofuran/glacial acetic acid/water mixture (35:65:10), and the mixture is stirred under argon for 6 hours. Thereafter the solvent is removed under vacuum at room temperature, the residue is dissolved in toluene, and the solution is distilled off. The crude product (60 mg) is purified by means of layer chromatography on four analytical thin-layer plates (company: Merck, 20×20 cm, layer thickness 0.25 mm) in a chloroform-ether (9:1) system, thus producing 54.4 mg of the 15α-alcohol (prostaglandin numbering).

IR: 3700, 2920, 1730, 1620 (weak), 1550, 1430, 1330, 1190, 1070, 970, 935, 795 cm$^{-1}$.

The 15β-alcohol epimer (64 mg) is treated analogously, thus obtaining 51 mg of the 11α,15β-diol.

IR: 3700, 2920, 1730, 1620 (weak), 1550, 1430, 1330, 1190, 1070, 970, 935, 795 cm$^{-1}$.

EXAMPLE 18

5-[(4R,5R)-4-[(3S)-(E)-3-Hydroxy-1-octenyl]-5-hydroxy-5,6-dihydro-4H-cyclopenta[b]furan-2-yl]pentanoic Acid (Furaprostacyclin) and 5-[(4R,5R)-4-[(3R)-(E)-3-Hydroxy-1-octenyl]-5-hydroxy-5,6-dihydro-4H-cyclopenta[b]furan-2-yl]pentanoic Acid A solution of 30.8 mg of the 11α, 15α-diol prepared in Example 17 in 1.6 ml of methanol is combined with 0.16 ml of 10% potassium hydroxide solution, and the mixture is stirred for 9 hours at room temperature under argon. Then the solvent is extensively concentrated under vacuum at 22° C. and the residue dissolved in 2.5 ml of water. The aqueous phase is extracted with ether, the organic phase is separated and discarded. The aqueous phase is acidified with 10% citric acid solution (pH 5-4.5) and extracted with ether. The ether solution is dried over magnesium sulfate and concentrated, thus obtaining 26 mg of the title compound (15α-alcohol epimer).

IR: 3900 (broad), 2950, 1720, 1620 (weak), 1550, 1430, 1330, 970 cm$^{-1}$.

The 11α,15β-diol methyl ester of Example 17 is saponified analogously in methanolic potassium hydroxide solution. Starting with 36 mg of ester, 28.5 mg of the title compound is produced (15β-alcohol epimer).

IR: 3900 (broad), 2950, 1720, 1620 (weak), 1550, 1430, 1330, 970 cm$^{-1}$.

EXAMPLE 19

5-[(4R,5R)-4-[(E)-(4RS)-3-Oxo-4-methyl-1-octenyl]-5-(tetrahydropyran-2-yloxy)-5,6-dihydro-4H-cyclopenta[b]furan-2-yl]pentanoic Acid Methyl Ester A suspension of 51 mg of sodium hydride (50% suspension in oil) in 8.5 ml of absolute dimethoxyethane is combined with a solution of 246 ml of dimethyl(2-oxo-3-methylheptyl)phosphonate (DOS No. 2,221,301) in 2.0 ml of absolute dimethoxyethane, and the mixture is stirred under argon for 0.5 hour at room temperature. The solution is cooled to −40° C., combined with a solution of 332 mg of the aldehyde described in Example 14 in 3.0 ml of absolute dimethoxymethane, and the mixture is stirred for 2 hours at −30° C. To the reaction solution is added dropwise 0.55 ml of glacial acetic acid in 3.0 ml of dimethoxyethane, and the mixture is then diluted with about 20 ml of ether. This solution is washed in succession with dilute sodium bicarbonate solution, water, and semisaturated sodium chloride solution, dried over magnesium sulfate, and concentrated under vacuum. The crude product is chromatographed over 20 g of silica gel with a hexane/20% ethyl acetate-hexane gradient. Yield: 271 mg of the title compound as an oil.

IR: 2940, 1740, 1670, 1640, 1550, 1430, 1340, 1200, 1130, 1070, 1030, 970 cm$^{-1}$.

EXAMPLE 20

5-[(4R,5R)-4-[(3S,4RS)-(E)-3-Hydroxy-4-methyl-1-octenyl]-5-hydroxy-5,6-dihydro-4H-cyclopenta[b]furan-2-yl]pentanoic Acid (16-Methylfuraprostacyclin)

Analogously to Example 16–18, starting with 260 mg of the α,β-unsaturated ketone obtained in Example 19, 66 mg of the title compound is obtained.

IR: 3900 (broad), 2950, 1720, 1620, 1540, 1430, 1330, 970 cm$^{-1}$.

EXAMPLE 21

5-[(4R,5R)-4-[(4RS)-(E)-3-Oxo-4-fluoro-1-octenyl]-5-(tetrahydropyran-2-yloxy)-5,6-dihydro-4H-cyclopenta[b]furan-2-yl]pentanoic Acid Methyl Ester A solution of 288 mg of dimethyl(2-oxo-3-fluoroheptyl)phosphonate (DOS No. 2,320,368) in 4.5 ml of absolute dimethoxyethane is introduced under agitation within 5 minutes at room temperature under argon to a suspension of 55 mg of sodium hydride (50% suspension in oil) in 12.0 ml of absolute dimethoxyethane. The solution is cooled to −30° C., combined with a solution of 420 mg of the aldehyde disclosed in Example 14 in 4.5 ml of absolute dimethoxyethane, and the mixture is stirred for 2 hours at −40° C. Then 0.60 ml of acetic acid in 4.0 ml of dimethoxyethane is added dropwise to the reaction solution, and the mixture is diluted with ether. The organic solution is washed in succession with dilute sodium bicarbonate solution, water, and semisaturated sodium chloride solution, dried over magnesium sulfate, and concentrated under vacuum. The crude product is chromatographed over 20 g of silica gel in a hexane/25% ethyl acetate-hexane gradient, thus obtaining 345 mg of the title compound.

IR (chloroform): 2950, 1720, 1700 (shoulder), 1625, 1550, 1430, 1330, 970 cm$^{-1}$.

EXAMPLE 22

5-[(4R,5R)-4-[(3R,4RS)-(E)-3-Hydroxy-4-fluoro-1-octenyl]-5-hydroxy-5,6-dihydro-4H-cyclopenta[b]furan-2-yl]pentanoic Acid Analogously to Examples 16–18, starting with 340 mg of the α,β-unsaturated ketone obtained in Example 21, 74 mg of the title compound is produced.

IR: 3900 (broad), 2950, 1720, 1620, 1540, 1430, 1320, 970 cm$^{-1}$.

EXAMPLE 23

5-[(4R,5R)-4-[(E)-3-Oxo-4-phenoxy-1-butenyl]-5-(tetrahydropyran-2-yloxy)-5,6-dihydro-4H-cyclopenta[b]furan-2-yl]pentanoic Acid Methyl Ester 405 mg of the lithium salt of dimethyl(2-oxo-3-phenoxypropyl)phosphonate (DOS No. 2,655,004) is introduced into a solution, cooled to −30° C., of 290 mg of the aldehyde disclosed in Example 14 in 18.5 ml of absolute tetrahydrofuran, and the solution is stirred for 1.5 hours under argon at this temperature. The solution is then allowed to warm up to 5° C. and 1.1 ml of acetic acid is added thereto. The solution is diluted with ether and washed in succession with dilute sodium bicarbonate solution, water, and semi-saturated sodium chloride solution. The organic phase is dried over magnesium sulfate and concentrated under vacuum. After purification of the crude product by chromatography over silica gel (20 g) in a hexane/20% ethyl acetate-hexane gradient, 303 mg of the title compound is obtained.

IR: 2940, 1730, 1670, 1630, 1600, 1540, 1430, 1330, 980, 760 cm$^{-1}$.

EXAMPLE 24

5-[(4R,5R)-4-[(3R)-(E)-3-Hydroxy-4-phenoxy-1-butenyl]-5-hydroxy-5,6-dihydro-4H-cyclopenta[b]furan-2-yl]pentanoic Acid Analogously to Example 16–18 starting with 300 mg of the α,β-unsaturated ketone obtained in Example 23, 62 mg of the title compound is produced.

IR: 3900 (broad), 2950, 1730, 1670, 1640, 1600, 1540, 1430, 1330, 980, 760 cm$^{-1}$.

EXAMPLE 25

5-[(4R,5R)-4-[(4RS)-(1E,6Z)-3-Oxo-4-methyl-7-chloro-1,6-octadienyl]-5-(tetrahydropyran-2-yloxy)-5,6-dihydro-4H-cyclopenta[b]furan-2-yl]pentanoic Acid Methyl Ester Within 10 minutes, 317 mg of dimethyl [(5Z)-2-oxo-3-methyl-6-chloro-5-heptenyl]phosphonate in 4.0 ml of absolute dimethoxymethane is added dropwise to a suspension of 57 mg of sodium hydride (50% in oil) in 12.0 ml of absolute dimethoxyethane, and the mixture is stirred, in total, for 0.5 hour at room temperature under argon. The solution is cooled to −40° C. and combined with a solution of 360 mg of the aldehyde described in Example 14. After 2 hours of agitation at −30° C., the mixture is neutralized with acetic acid and diluted with ether. The organic solution is washed in succession with dilute sodium bicarbonate solution, water and semisaturated sodium bicarbonate solution, water and semisaturated sodium chloride solution, dried over magnesium sulfate, and concentrated under vacuum. The residue is chromatographed over 25 g of silica gel in a hexane/15% acetone-hexane gradient, thus obtaining 285 mg of the title compound.

IR: 2930, 1740, 1660, 1630, 1540, 1420, 1340, 1200, 1130, 1070, 1030, 970 cm$^{-1}$.

Dimethyl[(5Z)-2-oxo-3-methyl-6-chloro-5-heptenyl]phosphonate, utilized in the above example, is prepared as follows:

(a) 2-[(2Z)-3-Chloro-2-butenyl]-2-methylmalonic Acid Diethyl Ester 11.5 g of sodium, cut into small pieces, is introduced into a three-necked flask equipped with agitator, reflux condenser, and dropping funnel. To this is added 250 ml of absolute ethanol so quickly that the solution boils vigorously. Thereafter 87 g of distilled methylmalonic acid diethyl ester is added dropwise to the hot alcoholate solution. After allowing the mixture to cool to about 75° C., the reaction solution is combined dropwise with 66 g of 1,3-dichloro-2-butene; the solution assumes a yellow color. After 2 hours of agitation under heating, the suspension which has a pH of 5–6 and at this point is almost completely decolorized, is freed of precipitated sodium chloride by filtration. The filtrate is concentrated and combined with the methylene chloride obtained by washing the precipitate. The organic solution is then shaken with saturated sodium chloride solution, dried over magnesium sulfate, concentrated with the use of a forced-circulation evaporator, and fractionated under vacuum, thus obtaining 105 g of the desired diester, bp$_{2.5}$ 110° C.

IR (film): 1738, 1666, 1160, 1050 cm$^{-1}$.

(b) 2-[(2Z)-3-Chloro-2-butenyl]-2-methylmalonic Acid 46 g of the diester obtained in the previous reaction stage is heated together with 33 g of potassium hydroxide in 85 ml of ethanol and 45 ml of water for 3.5 hours under reflux. After withdrawing the solvent under vacuum, the residue is taken up in 45 ml of water and acidified under ice cooling by dropwise addition of concentrated hydrochloric acid up to a pH of 1. The aqueous phase is then extracted five times by shaking. With respectively 200 ml of ether. The combined ether extracts are washed with saturated sodium chloride solution, dried over magnesium sulfate, and concentrated to dryness under vacuum. The residue is recrystallized from benzene/cyclohexane, thus obtaining 33.5 g of the di-acid, mp 99°–101° C.

IR (KBr): 2700, 2650, 2580, 1700, 1663, 1238 cm$^{-1}$.

(c) (4Z)-5-Chloro-2-methyl-4-hexenoic Acid 33.5 g of the dicarboxylic acid obtained in the preceding reaction stage is heated for 4 hours to 160° C. with CO$_2$ release. The product is then distilled under vacuum. Yield: 24.3 g of the monocarboxylic acid, bp$_{13}$ 133°–135° C.

IR (film): 2660, 2570, 1710, 1668, 1243 cm$^{-1}$.

(d) (4Z)-5-Chloro-2-methyl-4-hexenoic Acid Methyl Ester

In succession, 153 ml of N-ethyldiisopropylamine and 307 ml of iodomethane are added dropwise to a solution of 24.3 g of the carboxylic acid obtained according to the above directions in 450 ml of acetonitrile. After agitation for 4 hours at room temperature, the reaction solution is combined with ice-cold saturated sodium chloride solution and extracted with ethyl acetate. The combined organic phases are washed in succession with sodium bisulfate, sodium bicarbonate, and saturated sodium chloride solution, dried over sodium sulfate, and concentrated with the aid of a forced-circulation evaporator. The residue is distilled under vacuum, thus obtaining 21.9 g of the desired ester by isolation, bp$_{13}$ 81°–83° C.

IR (film): 1738, 1665, 1195, 1172 cm$^{-1}$.

(e) Dimethyl[(5Z)-2-oxo-3-methyl-6-chloro-5-heptenyl]phosphonate

Under argon at −60° C., 247.5 ml of a 2.02-molar butyllithium solution in hexane is added dropwise to a solution of 67.1 g of the methanephosphonic acid dimethyl ester described in Example 25(d) in 840 ml of absolute tetrahydrofuran. After 15 minutes, a solution of 44.16 g of the ester obtained according to the above directions in 100 ml of absolute tetrahydrofuran is added dropwise to the reaction mixture. The latter is maintained for 3.5 hours at −65° C., overnight at −32° C., and is finally allowed to warm up to room temperature. Then the mixture is combined with 28.6 ml of glacial acetic acid and concentrated to dryness under vacuum. The residue is distributed in a two-phase system of 175 ml of water and 825 ml of ether, the organic phase is dried over magnesium sulfate and concentrated on a forced-circulation evaporator. The evaporation residue is freed of volatile by-products and unreacted educt by distillation at 40° C./0.1 mm, and is then purified by column chromatography on silica gel with hexane/50–100% ethyl acetate as the eluent. Besides 13.8 g of educt, 36 g of phosphonate is obtained.

IR (film): 1712, 1666, 1260, 1032 $cm^{-1}$.

EXAMPLE 26

5-[(4R,5R)-4-[(3S,4RS)-(1E,6Z)-3-Hydroxy-4-methyl-7-chloro-1,6-octadienyl]-5-hydroxy-5,6-dihydro-4H-cyclopenta[b]furan-2-yl]pentanoic Acid Analogously to Example 16–18, 70 mg of the title compound is obtained, starting with 280 mg of the α,β-unsaturated ketone obtained in Example 25.

IR: 3900 (broad), 2950, 1720, 1620 (weak), 1550, 1430, 970 $cm^{-1}$.

EXAMPLE 27

5-[(4R,5R)-4-[(4RS)-(E)-3-Oxo-4,7-dimethyl-1,6-octadienyl]-5-(tetrahydropyran-2-yloxy)-5,6-dihydro-4H-cyclopenta[b]furan-2-yl]pentanoic Acid Methyl Ester Within 10 minutes, 510 mg of dimethyl(2-oxo-3,6-dimethyl-5-heptenyl)phosphonate in 9 ml of absolute dimethoxyethane is added dropwise to a suspension of 100 mg of sodium hydride (50% suspension in oil) in 22 ml of absolute dimethoxyethane, and the mixture is stirred under argon for 30 minutes at room temperature. The solution is cooled to −40° C. and combined with a solution of 600 mg of the aldehyde described in Example 14 in 9 ml of absolute dimethoxyethane. The mixture is stirred for 2 hours at −30° C. and subsequently combined with 1.1 ml of acetic acid and diluted with ether. After isolation and purification of the crude product as set forth in Example 21, 473 mg of the title compound is obtained.

IR: 2930, 1740, 1650, 1630, 1540, 1430, 1330, 1200, 1130, 1030, 970 $cm^{-1}$.

Dimethyl(2-oxo-3,6-dimethyl-5-heptenyl)phosphonate, utilized in the above example, is prepared as follows:

(a) 2-Ethoxycarbonyl-2,5-dimethyl-4-hexenoic Acid Ethyl Ester 36.1 g of sodium (cut into small pieces) is introduced into a three-necked flask equipped with reflux condenser, dropping funnel, and agitator. To this is added 800 ml of absolute ethanol dropwise so quickly that the solution keeps boiling vigorously. To the hot alcoholate solution is added dropwise 269.6 g of freshly distilled methylmalonic acid diethyl ester, the mixture is stirred for 0.5 hour at 60° C. and then—likewise in droplet form—241.7 g of dimethylallyl bromide is added thereto. After one hour of agitation with heating, the thus-precipitated sodium bromide is removed by filtering, the precipitate is washed, and the filtrate is concentrated. The residue is taken up in ether, washed neutral with saturated sodium chloride solution, dried over magnesium sulfate, and concentrated with the use of a forced-circulation evaporator. The evaporation residue is fractionated on an oil pump. *Yield: 266 g of the title compound, $bp_7$ 97°–112° C.

IR (film): 1735, 1245, 1025, 860 $cm^{-1}$.

(b) 2,5-Dimethyl-4-hexenoic Acid Ethyl Ester 85.3 g of 2-ethoxycarbonyl-2,5-dimethyl-4-hexenoic acid ethyl ester is dissolved in 645 ml of dimethyl sulfoxide and combined in succession with 29.7 g of lithium chloride and 6.3 ml of distilled water. Then the reaction mixture is heated for a total of 13 hours to 200° C. and then—after having been allowed to cool down—is poured on 1 liter of ice water. The aqueous phase is extracted three times with respectively 500 ml of methylene chloride. The combined organic extracts are then washed twice with water, dried over magnesium sulfate, concentrated with the aid of a forced-circulation evaporator, and distilled under vacuum, thus isolating 53.1 g, $bp_{13}$ 75°–78° C.

IR (film): 1735, 1160, 1050 $cm^{-1}$.

(c) Dimethyl(2-oxo-3,6-dimethyl-5-heptenyl)phosphonate

Under argon at −60° C., 474.7 ml of a 1.61-molar butyl-lithium solution in hexane is added dropwise to a solution of 59 g of methanephosphonic acid dimethyl ester in 400 ml of absolute tetrahydrofuran. After 15 minutes of agitation, a solution of 34.05 g of the 2,5-dimethyl-4-hexenoic acid ethyl ester described in Example 27(b) in 100 ml of absolute tetrahydrofuran is added dropwise thereto. The reaction mixture is allowed to warm up to room temperature within 4 hours and then stirred for another 3 hours. Thereafter the mixture is combined with 26.5 ml of glacial acetic acid and concentrated under vacuum. The residue is taken up in ether/water, the aqueous phase is combined with solid sodium chloride and extracted with ether. The combined organic phases are dried over magnesium sulfate and concentrated by using a forced-circulation evaporator. The evaporation residue is purified by column chromatography on silica gel with hexane/50–100% ethyl acetate as the eluent, thus obtaining 32 g of the title compound.

IR (film): 1710, 1260, 1030 $cm^{-1}$.

EXAMPLE 28

5-[(4R,5R)-4-[(3S,4RS)-(E)-3-Hydroxy-4,7-dimethyl-1,6-octadienyl]-5-hydroy-5,6-dihydro-4H-cyclopenta[b]furan-2-yl]pentanoic Acid Analogously to Examples 16–18, 111 mg of the title compound is obtained, starting with 465 mg of the α, -unsaturated ketone produced in Example 27.

IR: 3900 (broad), 2950, 1720, 1630, 1550, 1430, 1330, 970 $cm^{-1}$.

EXAMPLE 29

5-[(4R,5R)-4-[(3S)-(1E,5Z)-3-Hydroxy-1,5-octadienyl]-5-(tetrahydropyran-2-yloxy)-5,6-dihydro-4H-cyclopenta[b]furan-2-yl]pentanoic Acid Methyl Ester A solution of 904 mg of (2S)-(4Z)-2-hydroxy-4-heptenyltriphenylphosphonium bromide [E. J. Corey et al., J. Am. Chem. Soc. 93 (6) : 1490 (1971)] is cooled under argon to −70° C. and combined dropwise within 10 minutes with 3.2 ml of butyllithium solution (1.2-molar in hexane). The solution is heated to −30° C. and stirred at this temperature for 0.5 hour. To this mixture is added 480 mg of the aldehyde described in Example 14 in 5 ml of absolute tetrahydrofuran at −40° C., and the solution is further stirred for 1.5 hours. During this time, the reaction temperature is allowed to rise gradually to −25° C. The solution is then combined with 1 ml of acetic acid, diluted with ether, and the organic phase is washed in succession with dilute sodium bicarbonate solution, water, and semisaturated sodium chloride solution. The ether solution is dried over magnesium sulfate and concentrated under vacuum. The residue is chromatographed over 20 g of silica gel in a hexane/20% acetone-hexane gradient, thus obtaining 177 mg of the title compound. IR: 3940, 2930, 1730, 1640, 1550, 1430, 1340, 1210, 1130, 1070, 1030, 970 cm$^{-1}$.

EXAMPLE 30

5-[(4R,5R)-4-[(3S)-(1E,5Z)-3-Hydroxy-1,5-octadienyl]-5-hydroxy-5,6-dihydro-4H-cyclopenta[b]furan-2-yl]pentanoic Acid Analogously to Examples 17–18, starting with 170 mg of the alcohol produced according to Example 29, 81 mg of the title compound is obtained.

IR: 3900 (broad), 2950, 1720, 1630, 1550, 1430, 1340, 970 cm$^{-1}$.

EXAMPLE 31

5-[(4R,5R)-4-[(4RS)-(E)-3-Oxo-4-methyl-1-octen-6-ynyl]-5-tetrahydropyran-2-yloxy)-5,6-dihydro-4H-cyclopenta[b]furan-2-yl]pentanoic Acid Methyl Ester A suspension of 68 mg of sodium hydride (50% suspension in oil) in 9.5 ml of absolute dimethoxyethane is combined dropwise with 327 mg of dimethyl(2-oxo-3-methyl-5-heptynyl)phosphonate (DOS No. 2,729,960) in 4.5 ml of absolute dimethoxyethane within 10 minutes at room temperature under argon, and the mixture is stirred for 0.5 hour. Then the solution is cooled to −40° C. and combined with 430 mg of the aldehyde prepared according to Example 14 in 5 ml of absolute dimethoxyethane, and the mixture is stirred for 2 hours at −30° C. Thereafter 1.3 ml of acetic acid is added to the reaction mixture, the solution is diluted with ether, and the organic phase is washed in succession with dilute sodium carbonate solution, water, and semisaturated sodium chloride solution. The ether solution is dried over magnesium sulfate and concentrated under vacuum. The residue is chromatographed on silica gel in a hexane/15% ethyl acetate-hexane gradient, thus obtaining 364 mg of the title compound.

IR: 2930, 1730, 1670, 1630, 1550, 1430, 1340, 1120, 1030, 980 cm$^{-1}$.

EXAMPLE 32

5-[(4R,5R)-4-[(3S,4RS)-(E)-3-Hydroxy-4-methyl-1-octen-6-ynyl]-5-(tetrahydropyran-2-yloxy)-5,6-dihydro-4H-cyclopenta[b]furan-2-yl]pentanoic Acid Methyl Ester and 5-[(4R,5R)-4-[(3R,4RS)-(E)-3-Hydroxy-4-methyl-1-octen-6-ynyl]-5-(tetrahydropyran-2-yloxy)-5,6-dihydro-4H-cyclopenta[b]furan-2-yl]pentanoic Acid Methyl Ester Analogously to Example 16, reduction of 350 mg of the α,β-unsaturated ketone described in Example 31 with sodium borohydride yields 139 mg of the 15α-alcohol;

IR: 3950, 2940, 1730, 1630 (weak), 1540, 1430, 1340, 1210, 1060, 1030, 970 cm$^{-1}$, and 147 mg of the 15β-alcohol;

IR: 3950, 2940, 1730, 1630 (weak), 1540, 1430, 1340, 1210, 1060, 1030, 970 cm$^{-1}$.

EXAMPLE 33

5-[(4R,5R)-4-[(3S,4RS)-(E)-3-Hydroxy-4-methyl-1-octen-6-ynyl]-5-hydroxy-5,6-dihydro-4H-cyclopenta[b]furan-2-yl]pentanoic Acid and 5-[(4R,5R)-4-[(3R,4RS)-(E)-3-Hydroxy-4-methyl-1-octen-6-ynyl]-5-hydroxy-5,6-dihydro-4H-cyclopenta[b]furan-2-yl]pentanoic Acid Analogously to Examples 17–18, starting with 135 mg of the 11-tetrahydropyranyl ether 15α-ol described in Example =, 106 mg of the title compound (11α,15α-diol) is obtained;

IR: 3900 (broad), 2950, 1720, 1620 (weak), 1540, 1430, 1330, 1210, 970 cm$^{-1}$.

Under analogous conditions, starting with 147 mg of the 11-tetrahydropyranyl ether 15β-ol described in Example 32, 95 mg of the title compound (11α,15β-diol) is produced.

EXAMPLE 34

5-[(4R,5R)-4-[(4RS)-(E)-3-Oxo-4-methyl-1-nonen-7-ynyl]-5-(tetrahydropyran-2-yloxy)-5,6-dihydro-4H-cyclopenta[b]furan-2-yl]pentanoic Acid Methyl Ester Analogously to Example 31, a solution of the sodium salt of dimethyl(2-oxo-3-methyl-6-octynyl)phosphonate is prepared by treating a suspension of 56 mg of NaH (50% suspension in oil) in absolute dimethoxyethane (10 ml) with 286 mg of dimethyl(2-oxo-3-methyl-6-octynyl)phosphonate (DOS No. 3,048,906) in 5 ml of absolute dimethoxyethane. This solution is combined with 360 mg of the aldehyde produced according to Example 14, thus obtaining, after isolation and purification of the crude product, 184 mg of the title compound.

IR: 2940, 1740, 1670, 1630, 1550, 1430, 1340, 1120, 1030, 980 cm$^{-1}$.

EXAMPLE 35

5-[(4R,5R)-4-[(3S,4RS)-(E)-3-Hydroxy-4-methyl-1-nonen-7-ynyl]-5-hydroxy-5,6-dihydro-4H-cyclopenta[b]furan-2-yl]pentanoic Acid Analogously to Examples 16–18, starting with 180 mg of the α,β-unsaturated ketone described in Example 34, 44 mg of the title compound is obtained.

IR: 3900 (broad), 2940, 1725, 1620 (weak), 1550, 1430, 1330, 970 cm$^{-1}$.

EXAMPLE 36

5-[(4R,5R)-4-[(3S)-(E)-3-Hydroxy-1-octenyl]-5-hydroxy-5,6-dihydro-4H-cyclopenta[b]furan-2-yl]-pentanoic Acid Tris(hydroxymethyl)aminomethane Salt A solution of 35 mg of the 11α,15α-dihydroxy acid described in Example 18 in 2.0 ml of acetonitrile is heated under argon to 40° C. and combined with a solution of 12 mg of tris(hydroxymethyl)aminomethane in 0.2 ml of water. The mixture is stirred overnight at room temperature and then the solution is concentrated to dryness under vacuum, thus obtaining 47 mg of the title compound.

EXAMPLE 37

5-[(4R,5R)-4-[(3S,4RS)-(E)-3-Hydroxy-4-methyl-1-octenyl]-5-hydroxy-5,6-dihydro-4H-cyclopenta[b]-furan-2-yl]pentanoic Acid Methylsulfonylamide A solution of 37 mg of the acid produced according to Example 20 in 0.3 ml of pyridine is combined with 0.1 ml of acetic anhydride, and the mixture is stirred under argon at room temperature for 15 hours. The solution is concentrated under vacuum, and the residue is dissolved in 1.5 ml of acetonitrile. To this solution are added 12 mg of triethylamine and a solution of 16 mg of methylsulfonyl isocyanate in 0.8 ml of acetonitrile. After 4 hours of agitation at room temperature, the solution is poured into water (2 ml), and the aqueous phase is neutralized with 10% citric acid solution. This solution is extracted with ether, the organic phase is washed with semisaturated sodium chloride solution, dried over magnesium sulfate, and concentrated under vacuum. The residue is purified by means of preparative layer chromatography on three silica gel instant plates (company: Merck, 20×20 cm, layer thickness 0.25 mm) in ether as the eluent, thus obtaining 33 mg of the methylsulfonamide. The acetate blocking groups are removed by interesterification in methanol (1 ml)/potassium carbonate (30 mg). After 3 hours of stirring under argon, the methanol solution is neutralized and diluted with methylene chloride. The organic phase is washed with semisaturated sodium chloride solution, dried over magnesium sulfate, and concentrated. The residue is purified by means of preparative layer chromatography on two instant plates (as above) in chloroform-ethanol 9:1 as the eluent, thus obtaining 20 mg of the title compound as an oil.

IR (CHCl$_3$): 3400, 1720 (broad), 1550, 1430, 1340, 975 cm$^{-1}$.

EXAMPLE 38

5-[(4R,5R)-4-[(3S,4RS)-(E)-3-Hydroxy-4-methyl-1-octen-6-ynyl]-5-hydroxy-5,6-dihydro-4H-cyclopenta[b]furan-2-yl]pentanoic Acid Potassium Salt A solution of 60 mg of the prostacyclin derivative described in Example 33 is dissolved in 1.5 ml of methanol and combined under argon with 1.56 ml of 0.107-molar potassium hydrazide solution. The solution is stirred for 15 minutes and then concentrated under vacuum at room temperature, yielding 64 mg of the title compound as a white powder, mp 42°–51° C.

We claim:

1. A prostacyclin derivative of the formula

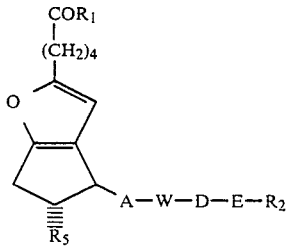

wherein
R$_1$ is OR$_3$, wherein R$_3$ is hydrogen; alkyl of 1–10 C-atoms; alkyl of 1–10 carbon atoms substituted by halogen, C$_{6-10}$-aryl, C$_1$–C$_4$-alkoxy, or C$_1$–C$_4$-dialkylamino; C$_{4-10}$-cycloalkyl; C$_{6-10}$-aryl; or an aromatic heterocyclic group of 5- or 6-ring atoms, one of which is O, N or S; or R$_1$ is NHR$_4$, wherein R$_4$ is hydrogen, C$_{1-10}$-alkanoyl, or C$_{1-10}$-alkanesulfonyl A is —CH$_2$—CH$_2$— or trans—CH=CH—, W is

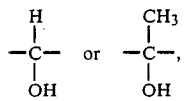

wherein each OH-group can be esterified with benzoyl or an alkanoic acid residue of 1–4 carbon atoms, or can be esterified with tetrahydropyranyl, tetrahydrofuranyl, C$_1$–C$_4$-alkoxyalkyl, or tri-(C$_1$–C$_4$-alkyl)-silyl, wherein the free, etherified or esterified OH-group can be in the α- or β-position, D and E jointly mean a direct bond or
D is alkylene or alkenylene or up to 5 carbon atoms, optionally substituted by F or C$_{1-4}$-alkyl,
E is an oxygen atom or a direct bond,
R$_2$ is alkyl of 1–6 carbon atoms, or alkenyl of 2–6 carbon atoms, both of which can be substituted by phenyl, halogen, or C$_1$–C$_4$-alkyl, and, if D and E jointly represent a direct bond, R$_2$ can be an alkynyl residue of 2–6 carbon atoms, optionally substituted in the 1-position by halogen or C$_1$–C$_4$-alkyl,
R$_5$ is hydrogen which can be esterified with an alkanoic acid residue of 1–4 carbon atoms or which can be etherified with a tetrahydropyranyl, tetrahydrofuranyl, alkoxyalkyl, or trialkylsilyl residue,
or if R$_3$ is hydrogen, a salt thereof with a physiologically compatible base.

2. A compound of claim 1 wherein D and E are a direct bond and R$_2$ is alkenyl or alkynyl.

3. A compound of claim 2 wherein the double or triple bond in R$_2$ is in the 17,18- or 18,19- position of the prostacyclin.

4. 5-[(4R,5R)-4-[(3S)-(E)-3-Hydroxy-1-octenyl]-5-(tetrahydropyran-2-yloxy)-5,6-dihydro-4H-cyclopenta[b]-furan-2-yl]pentanoic acid methyl ester, a compound of claim 1.

5. 5-[(4R,5R)-4-[(3R)-(E)-3-Hydroxy-1-octenyl]-5-(tetrahydropyran-2-yloxy)-5,6-dihydro-4H-cyclopenta[b]-furan-2-yl]pentanoic acid methyl ester, a compound of claim 1.

6. 5-[(4R,5R)-4-[(3S)-(E)-3-Hydroxy-1-octenyl]-5-hydroxy-5,6-dihydro-4H-cyclopenta[b]furan-2-yl]pentanoic acid methyl ester, a compound of claim 1.

7. 5-[(4R,5R)-4-[(3R)-(E)-3-Hydroxy-1-octenyl]-5-hydroxy-5,6-dihydro-4H-cyclopenta[b]furan-2-yl]pentanoic acid methyl ester, a compound of claim 1.

8. 5-[(4R,5R)-4-[(3S)-(E)-3-Hydroxy-1-octenyl]-5-hydroxy-5,6-dihydro-4H-cyclopenta[b]furan-2-yl]pentanoic acid, a compound of claim 1.

9. 5-[(4R,5R)-4-[(3R)-(E)-3-Hydroxy-1-octenyl]-5-hydroxy-5,6-dihydro-4H-cyclopenta[b]furan-2-yl]pentanoic acid, a compound of claim 1.

10. 5-[(4R,5R)-4-[(3S,4RS)-(E)-3-Hydroxy-4-methyl-1-octenyl]-5-hydroxy-5,6-dihydro-4H-cyclopenta[b]furan-2-yl]pentanoic acid, a compound of claim 1.

11. 5-[(4R,5R)-4-[(3R,4RS)-(E)-3-Hydroxy-4-fluoro-1-octenyl]-5-hydroxy-5,6-dihydro-4H-cyclopenta[b]furan-2-yl]pentanoic acid, a compound of claim 1.

12. 5-[(4R,5R)-4-[(3R)-(E)-3-Hydroxy-4-phenoxy-1-butenyl]-5-hydroxy-5,6-dihydro-4H-cyclopenta[b]furan-2-yl]-pentanoic acid.

13. 5-[(4R,5R)-4-[(3S,4RS)-(1E,6Z)-3-Hydroxy-4-methyl-7-chloro-1,6-octadienyl]-5-hydroxy-5,6-dihydro-4H-cyclopenta[b]furan-2-yl]pentanoic acid, a compound of claim 1.

14. 5-[(4R,5R)-4-[(3S,4RS)-(E)-3-Hydroxy-4,7-dimethyl-1,6-octadienyl]-5-hydroxy-5,6-dihydro-4H-cyclopenta[b]furan-2-yl]pentanoic acid, a compound of claim 1.

15. 5-[(4R,5R)-4-[(3S)-(1E,5Z)-3-Hydroxy-1,5-octadienyl]-5-(tetrahydropyran-2-yloxy)-5,6-dihydro-4H-cyclopenta[b]furan-2-yl]pentanoic acid methyl ester, a compound of claim 1.

16. 5-[(4R,5R)-4-[(3S)-(1E,5Z)-3-Hydroxy-1,5-octadienyl]-5-hydroxy-5,6-dihydro-4H-cyclopenta[b]furan-2-yl]pentanoic acid.

17. 5-[(4R,5R)-4-[(3S,4RS)-(E)-3-Hydroxy-4-methyl-1-octen-6-ynyl]-5-(tetrahydropyran-2-yloxy)-5,6-dihydro-4H-cyclopenta[b]furan-2-yl]pentanoic acid methyl ester.

18. 5-[(4R,5R)-4-[(3R,4RS)-(E)-3-Hydroxy-4-methyl-1-octen-6-ynyl]-5-(tetrahydropyran-2-yloxy)-5,6-dihydro-4H-cyclopenta[b]furan-2-yl]pentanoic acid methyl ester.

19. 5-[(4R,5R)-4-[(3S,4RS)-(E)-3-Hydroxy-4-methyl-1-octen-6-ynyl]-5-hydroxy-5,6-dihydro-4H-cyclopenta[b]furan-2-yl]pentanoic acid.

20. 5-[(4R,5R)-4-[(3R,4RS)-(E)-3-Hydroxy-4-methyl-1-octen-6-ynyl]-5-hydroxy-5,6-dihydro-4H-cyclopenta[b]furan-2-yl]pentanoic acid.

21. 5-[(4R,5R)-4-[(3S,4RS)-(E)-3-Hydroxy-4-methyl-1-nonen-7-ynyl]-5-hydroxy-5,6-dihydro-4H-cyclopenta[b]furan-2-yl]pentanoic acid.

22. 5- (4R,5R)-4-[(3S)-(E)-3-Hydroxy-1-octenyl]-5-hydroxy-5,6-dihydro-4H-cyclopenta[b]furan-2-yl]pentanoic acid tris(hydroxymethyl)aminomethane salt.

23. 5-[(4R,5R)-4-[(3S,4RS)-(E)-3-Hydroxy-4-methyl-1-octenyl]-5-hydroxy-5,6-dihydro-4H-cyclopenta[b]furan-2-yl]pentanoic acid methylsulfonylamide.

24. 5-[(4R,5R)-4-[(3S,4RS)-(E)-3-Hydroxy-4-methyl-1-octen-6-ynyl]-5,6-dihydro-4H-cyclopenta[b]furan-2-yl]pentanoic acid potassium salt.

25. A pharmaceutical composition comprising at least one compound according to claim 1, in an amount effective for lowering of blood pressure of inhibition of thrombocyte aggregation and a pharmaceutically acceptable carrier.

26. A method of lowering blood pressure in a patient comprising administering an amount of a compound of claim 1 effective to lower blood pressure.

* * * * *